Figure 1:
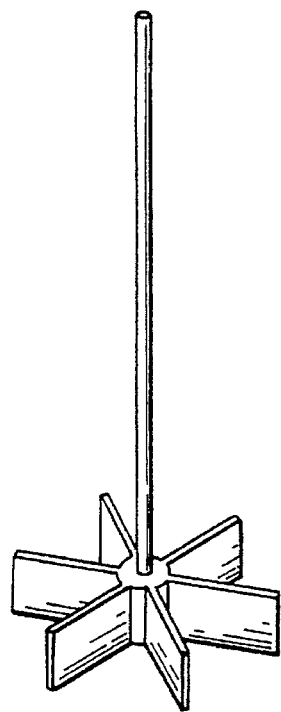
Figure 2:
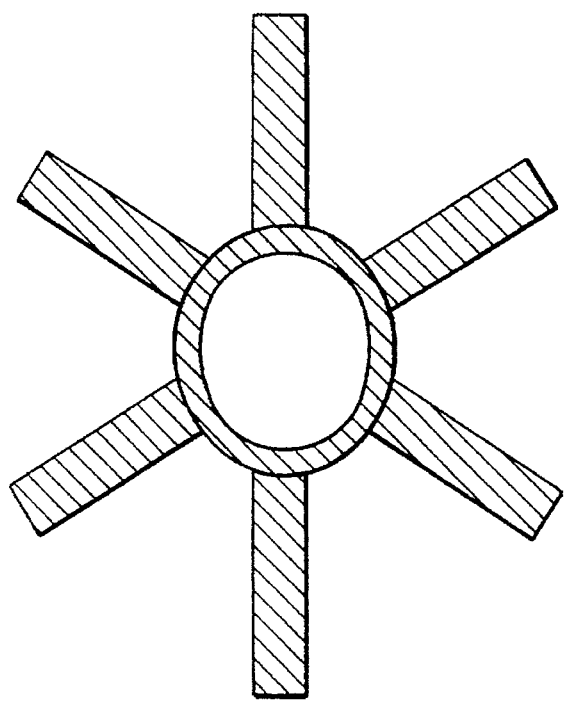

United States Patent [19]
Illum et al.

[11] Patent Number: 5,648,095
[45] Date of Patent: Jul. 15, 1997

[54] PREPARATION OF MICROPARTICLES

[75] Inventors: Lisbeth Illum, The Park, United Kingdom; Olufunmiloyo Lilly Johnson, Cambridge, Mass.

[73] Assignee: Danbiosyst UK Limited, Nottingham, United Kingdom

[21] Appl. No.: 190,022

[22] PCT Filed: Aug. 3, 1992

[86] PCT No.: PCT/GB92/01421

§ 371 Date: Jul. 8, 1994

§ 102(e) Date: Jul. 8, 1994

[87] PCT Pub. No.: WO93/02712

PCT Pub. Date: Feb. 18, 1993

[30] Foreign Application Priority Data

Aug. 1, 1991 [GB] United Kingdom ............ 9116610

[51] Int. Cl.$^6$ ............................... A61K 9/50; A61K 9/66
[52] U.S. Cl. ..................... 424/489; 424/499; 424/501; 264/4.1; 264/4.3; 264/4.33; 264/4.6
[58] Field of Search ....................... 424/489, 499, 424/501, 490–498; 264/4.1, 4.3, 4.33, 4.6

[56] References Cited

U.S. PATENT DOCUMENTS

| | | | |
|---|---|---|---|
| 3,781,230 | 12/1973 | Vassiliades et al. | 106/213 |
| 4,089,800 | 5/1978 | Temple | 252/316 |
| 4,173,488 | 11/1979 | Vasiliades et al. | 260/2.5 B |
| 4,713,249 | 12/1987 | Schroder | 424/488 |
| 5,195,520 | 3/1993 | Schlief | 128/660.02 |
| 5,271,961 | 12/1993 | Mathiowitz | 427/213.31 |

FOREIGN PATENT DOCUMENTS

| | | |
|---|---|---|
| 0213303 | 3/1987 | European Pat. Off. . |
| 0324938 | 7/1989 | European Pat. Off. . |
| 327490 | 8/1989 | European Pat. Off. . |
| 0398935 | 8/1989 | European Pat. Off. . |
| 0458745 | 11/1991 | European Pat. Off. . |
| 2233095 | 1/1975 | France . |
| 2285147 | 4/1976 | France . |
| 1288583 | 9/1972 | United Kingdom . |
| 8400294 | 2/1984 | WIPO . |
| 9013540 | 11/1990 | WIPO . |
| 9112823 | 9/1991 | WIPO . |

OTHER PUBLICATIONS

Schroeder, U., Stahl,A. and Salford, L.G. in Microspheres and Drug Therapy, Pharmaceutical, Immunological and Medical Aspects. Davis et.al. Editors, Elsevier, Amsterdam, pp. 427–435 (1984).

Mosbach, K and Schroeder, U. in Enzeyme Eng. 5 239–41 (1980).

*Primary Examiner*—Gollamudi S. Kishore
*Attorney, Agent, or Firm*—Arnall Golden & Gregory

[57] ABSTRACT

Hollow microcapsules or solid microspheres for use in diagnostic procedures, as well as methods for making the microcapsules, are provided, which are formed by combining a volatile oil with an aqueous phase including a water soluble material such as a starch, modified starch or proteinaceous material, or a polyethylene glycol (PEG) conjugate, to form a primary emulsion. The primary emulsion then is combined with a second oil, to form a secondary emulsion, and the material is permitted to harden and to form microcapsules around a liquid core of the volatile oil. At least part of the volatile oil then may be removed by evaporation to produce hollow microcapsules. Optionally, all of the volatile oil may be removed prior to hardening of the material, which produces solid microspheres. The The microcapsules can be used in a variety of applications for diagnostic purposes and for drug delivery.

16 Claims, 1 Drawing Sheet

PREPARATION OF MICROPARTICLES

The present invention relates to microparticles and their preparation, and more particularly to drug carriers for intranasal and intravaginal administration and to diagnostic aids, particularly echogenic materials for echocardiography and other purposes.

Microparticles, in the form of microspheres and microcapsules are well described in the pharmaceutical literature (for example, see the book, "Microspheres and Drug Therapy, Pharmaceutical Immunological and Medical Aspects", edited by S. S. Davis, L. Illum, J. G McVie and E. Tomlinson, Elsevier, Amsterdam, 1984). Such systems can be used as carriers for drugs and vaccines as diagnostic agents, and in surgical procedures (embolisation). Other applications can be identified in the field of cosmetics. The sizes of these microparticles can range from hundreds of microns to a few nanometres depending upon the application. Microparticulate drug delivery systems can be administered by a wide variety of routes but in particular, into the blood stream, into the muscle or subcutaneous space, into compartment of the body such as the pleura, into joints, into the eye, the respiratory system (nose and lungs), the gastrointestinal tract (to include buccal and rectal administration) and into the genitourinary tract (bladder instillation, vaginal administration).

It is known from EP-A-324-938 that air filled albumin microcapsules of about 1–10 μm can be injected into the blood stream and will reflect ultrasonic radiation in such a way as to yield diagnostically useful images. These microbubbles are formed by first preparing microbubbles through a process of sonicating viscous albumin solutions. The resulting microbubbles are heat denatured to render the albumin water insoluble.

Starch is a natural microparticulate with a size in the 5 to 20 micron range. For more than a century, this material has been used as a pharmaceutical excipient. It has low immunogenicity and is biodegradable. Starch can be modified physically and chemically. This modification can conserve or destroy the granular nature of starch or can cause modifications at the molecular level. The properties of starch and derivatives thereof have been described in detail by Wurzburg, M. S. "Modified Starches, Properties and Uses", CRC Press, Boca Raton, 1986 and Gaillard, T. (Editor) "Starch: Properties and Potential", Critical reports on Applied Chemistry vol. 13, John Wiley, Chichester, 1987.

Mosbach, K. and Schroëder, U. in Enzyme Eng. 5 239–41 (1980) describe the preparation of magnetic microspheres where acid hydrolysed starch suspended together with magnetic material is poured into toluene containing a surfactant to give beads having a mean diameter of about 10 micron. The preparation of crystallized carbohydrate spheres has been described by Schroëder, U., Ståhl, A. and Salford, L. G. in Microspheres and Drug Therapy, Pharmaceutical, Immunological and Medical Aspects, Davis, S. S. et al Editors, Elsevier, Amsterdam, 1984, p. 427 and Schroëder, U. PCT/SE83/00268, 1983 (WO84/00294). Here, an aqueous carbohydrate solution is thoroughly mixed with substances to be entrapped and an emulsifying medium (corn, rape seed or cottonseed oil) added and an emulsion formed. This emulsion is then poured slowly into acetone containing a small concentration of non-ionic surface active agent. The carbohydrate spheres then precipitate and can be collected.

Ekman, B. M. and Lindahl, A. R. have used two immiscible aqueous phases to produce starch microspheres (EP-A-213303). The small spherical particles were produced by solidification of the dispersed droplets of a moderately soluble material (eg starch, agar, gelatin, pectin, collagen, carrageenin, fibrin), in a continuous phase of a second immiscible aqueous phase.

The formation of microcapsules by a double emulsion process from non-carbohydrate non-biodegradable materials has been proposed previously GB-A-1 288 583 for the preparation of organic pigment microcapsule for use in paints. The polymers used were insoluble polymers like polystyrene and there was no suggestion of the use of the microcapsules for pharmaceutical, biomedical or cosmetic applications nor for nasal administration or as an injectable composition for echocardiography, whereas the compositions of the present invention, at least when used for such a purpose, are biocompatible, biodegradable and non-immunogenic. U.S. Pat. No. 3,919,110 describes substantially spherical air containing microcapsules having an average diameter of about 2 microns. Precursor microcapsules were prepared using a simple oil in water emulsification method where the aqueous phase contained a dispersion of a partially condensed formaldehyde condensation product being capable of being separated from the aqueous phase in solid particle form upon dilution with water. Hydrophobic starch was used as a preferred emulsifying agent. Here, again, there was no suggestion that such particles could be used for pharmaceutical, biomedical or cosmetic applications such as nasal administration or as an injectable composition for echocardiography.

A. Kondo in "Microcapsule Processing and Technology" (Marcel Dekker Inc, New York, 1979) suggests forming hollow capsules using a low boiling point solvent as the core in an in-liquid drying process (page 109) and oil-containing gelatin capsules from which the oil is not subsequently removed. U.S. Pat. No. 4,173,488, U.S. Pat. No. 3,781,230 and U.S. Pat. No. 4,089,800 disclose the use of hydrophobic resins and hydrophobic starches to coat the oil droplets in an oil-in-water emulsion and subsequently form microcapsules. None of these documents mentions using the microcapsules for echocardiography. EP-A-0 327 490 discloses the use of synthetic polymers to surround gas bubbles in a liquid medium and subsequently form microcapsules for echocardiography. This is a different process from that of the present invention.

We have now devised an improved process for preparing hollow microcapsules from a water-soluble starch derivative or a PEG-modified material and also for preparing solid microspheres.

One aspect of the invention provides a process for preparing solid microspheres or air-filled microcapsules comprising forming initial microcapsules containing a liquid core, and removing at least some of the said liquid to create either solid microspheres or air-filled microcapsules, provided that the wall-forming material used for the air-filled microcapsules is a water-soluble starch derivative other than hydroxyethyl starch, or a PEG-modified material.

By a "PEG-modified material" we mean any material which has been modified by conjugation with polyethylene glycol and is suitable for forming the microcapsules or microspheres, or a mixture of such a PEG-modified material with a suitable unmodified material, and reference to any PEG-modified material is used to include such mixtures.

The core in the process of the present invention is preferably a water-immiscible oil and is preferably also relatively volatile so that it can be evaporated after the microcapsules have been formed, in other words during or after the hardening of the wall. This is what we mean by "relatively volatile". More specifically, any inert oil, preferably a perfluoro compound, having a boiling point of 20°–100° C., preferably 40°–90° C. and more preferably 50°–80° C. is generally suitable. Perfluorohexane, perfluoroheptane, perfluoromethylcyclohexane, cyclopentane, hexane, 2-methylpentane, 3-methylpentane, 2,2-dimethylbutane, 2,3-dimethylbutane, 1-chloropropane, 2-chloro-2-methyl propane, chloroform, methylene chloride, 1,1-dichloroethane and bromoethane are all suitable. More than one core can be provided in each microcapsule.

The process for the production of the hollow microcapsules or solid microspheres may be any of those generally known as simple coacervation, complex coacervation, MSIEP (minimisation of solubility at isoelectric point) and double emulsion, but is preferably the latter. Interfacial polymerisation may be used for some wall-forming materials, although not for proteinaceous materials.

The double emulsion method is particularly preferred for formation of both the hollow air-filled microcapsules and the solid microspheres. In the preparation of solid microspheres, the amount of oil used in the primary emulsion is less than that used in the preparation of hollow microcapsules and is typically 0.5–10 ml. A small volume of oil, such as perfluorohexane, is required to prevent the inclusion of soya oil, the oil phase of the secondary emulsion, in the solid microspheres. The inclusion of soya oil or similar vegetable oil used in the secondary emulsification process into the core of the microspheres makes dispersion in an aqueous medium difficult and inefficient and could well preclude the use of such microparticles in a dried form for subsequent reconstitution before administration. This small volume of oil used in the primary emulsion is evaporated before the initial microcapsules have become fully set, thus forming solid microspheres as the final product.

Any suitable soluble starch derivative may be used as the wall forming material for the hollow microcapsules provided it is soluble in water but which can be rendered water-insoluble once the microcapsules are made. Amylodextrin, amylopectin and carboxymethyl starch are particularly preferred. For human use, amylodextrin is preferred. This can be prepared by treatment of potato or corn starch with diluted hydrochloric acid by known techniques.

Starch (or its derivatives) modified with polyethylene glycol to produce a PEG-starch conjugate may be used to produce hollow microcapsules or solid microspheres with PEG groups at their surface that may endow such microspheres with long circulation times in vivo. (Illum & Davis, J. Pharm. Sci. 72, 1983, 1086–1089; Illum and Davis, FEBS Lett., 167, 1984, 79–82). PEG-starch (or starch derivative) may be used by itself or in combination with unmodified starch derivative or albumin. The grafting of polyethylene glycol on carbohydrates has been described Corretge et al., Polym. Med., III, Edited by C. Migliaresi et al., Elsevier, Amsterdam, 1988, pp 61–72.

Albumin modified by conjugation to polyethylene glycol as described in various publications and patents (for reviews see for example Harris, Macromol. Chem. Phys. C25, 1985, 325–373; Inada et al., J. Bioact. Compat. Polym., 5, 1990, 343–364; Pizzo, Adv. Drug Del. Rev., 6, 1991, 153–166; Fuertges and Abuchowski, J. Cont. Rel., 11, 1990, 139–148; Nucci et al., Adv. Drug Del. Rev., 6, 1991, 123–151) can also be used for the production of the hollow microcapsules and solid microspheres prepared according to the present invention. Albumin-PEG can either be used by itself or in combination with unmodified albumin or starch derivative. Such microspheres have PEG groups at their surface and as a result will display enhanced circulation times as described by Illum (Illum and Davis, J. Pharm. Sci., 72, 1983, 1086–1089; Illum and Davis, FEBS Lett., 167, 1984, 79–82).

The PEG used in the present invention preferably has a molecular weight of 200–10000 and more preferably 1000 to 6000.

The process of conjugating PEG to materials such as albumin or starch, or PEGylation as the process is known in the art, is described in detail in U.S. Pat. No. 4,179,337, incorporated herein by reference. The PEG may be activated for conjugation by any method known in the art, for example a N-hydroxysuccinimide derivative of PEG may be prepared and used.

The amount of conjugation of the albumin or starch (or its derivatives) is between 1% and 90% and is preferably between 5% and 50%.

Any suitable wall-forming material may be used for the solid microspheres which is (i) dispersible (preferably soluble) in water, (ii) capable of being rendered water-insoluble once the microcapsules are made and (iii) physiologically non-toxic and non-immunogenic, at least in the conditions of use. Materials which are biodegradable in the patient following administration are preferred. Proteinaceous materials such as serum albumin are suitable The term "proteinaceous" is used herein to describe proteins, naturally-occurring and synthetic polypeptides and fragments of proteins and polypeptides. Other materials include gelatin, starch and dextran. Soluble starch derivatives are preferred, and amylodextrin, amylopectin, carboxymethyl starch and hydroxyethyl starch are particularly preferred. The properties of some materials, such as albumin, may be modified by the presence of an added non-ionic surfactant, such as is described by Omotosho et al as interfacial complexation (1986 J. Pharm. Pharmacol. 38, 865–870). The materials are chemically or thermally denatured, to render them insoluble, after the microcapsules have been formed.

The material can be made water-insoluble by chemical cross-linking, denaturation (for example with heat), chelating or grafting.

The hollow microcapsules of the invention are filled with a gas or vapour, which may be air or any other true gas but is often a mixture of air and the vapour from the volatile oil. In this specification, the terms "air-filled" and "gas-filled" are both loosely used to cover pure air, any other gas, any vapour or mixtures thereof. The air content of the microcapsules can be varied by changing the phase volume of oil in the primary emulsion in the range of 0.5 ml–100 ml. In addition, the phase volume of the oil phase in the primary emulsion can be reduced to increase the proportion of solid microspheres formed.

The solid microspheres and hollow microcapsules which are formed are preferably from 0.1 to 500 μm in diameter. For nasal and intravaginal delivery, particles in the size range 1 to 100 μm in diameter are to be preferred. For the hollow microcapsule for use in echocardiography, a range of 1.0 to 10 μm is preferred and 2.0 to 8 μm is especially suitable. Such sizes may be achieved by appropriately selecting the process parameters and/or by separating out, for example by sieving, the desired size from the resulting microcapsules. Since a range of sizes will usually result, the figures in this specification refer to 90% of the population by weight. The size range can be measured with a light microscope or by using known size measuring apparatus such as the Coulter Counter and laser diffractometer.

A multi-chamber microcapsule may result, resembling a honeycomb or a single chamber, ie a shell. There may be from one to several hundred chambers in each microcapsule.

The final product is typically obtained in the form of a suspension which may be washed, sterilised and used. In at least some cases, however, the microcapsules can be freeze-dried without collapsing and stored as a free-flowing powder for future use.

Mixed systems containing both solid microspheres and hollow microcapsules can be used as such or separated if necessary using flotation or centrifugation with density gradients if required.

The air-filled microcapsules may be used in echocardiography and other ultrasonic imaging techniques in ways known in the art, in nasal and lung delivery systems for drugs (when prepared as powder, rather than suspensions) and as opacifiers or reflectivity enhancers in cosmetics.

The air-filled microcapsules themselves and their uses, particularly as echogenic materials in diagnostic procedures, form further aspects of the invention.

The solid microspheres may be used as drug delivery systems for nasal, oral, pulmonary and vaginal delivery. They are of particular use in nasal delivery systems and may be used to delivery drugs such as;

Polypeptides or their derivatives (preferably with a molecular weight from 1000 to 300,000)
Insulin (hexameric/dimeric/monomeric forms)
Glucagon
Somatostatin
Growth Hormone
Calcitonins and synthetic modifications thereof
Enkephalins
Interferons (especially Alpha-2 Interferon for treatment of common colds)
LHRH and analogues (Nafarelin, Buserelin, Goserelin)
GHRH (Growth hormone releasing hormone)
Secretin
CCK (Cholesytekinin)
Bradykin antagonists
GRF (Growth releasing factor)
THF
TRH (Thyrotropin releasing hormone)
ACTH analogues
CSFs (colony stimulating factors)
EPO (Erythropoetin)
IGF (Insulin like growth factors)
CGRP (Calcitonin gene related peptide)
Atrial Natriuretic Peptide
Vasopressin and analogues (DDAVP, Lypressin)
other drugs include:
  Antibiotics
  Metoclopramide
  Migraine treatment (Dihydroergotamine, Ergometrine, Ergotamine, Pizotizin)
  Vaccines (Particularly AIDS vaccines)

Factor VIII

Low Molecular Weight Heparins

Antibiotics and antimicrobial agents such as tetracycline hydrochloride, leucomycin, penicillin, penicillin derivatives and erythromycin, chemotherapeutic agents such as sulphathiazole and nitrofurazone; local anaesthetics such as benzocaine; vasoconstrictors such as phenylephrine hydrochloride, tetrahydrozoline hydrochloride, naphazoline nitrate, oxymetazoline hydrochloride and tramazoline hydrochloride; cardiotonics such as digitalis and digoxin; vasodilators such as nitroglycerin and papaverine hydrochloride; antiseptics such as chlorhexidine hydrochloride, hexylresorcinol, dequalinium chloride and ethacridine; enzymes such as lysozyme chloride, dextranase; bone metabolism controlling agents such as vitamin $D_3$ and active vitamin $D_3$; sex hormones; hypotensives; sedatives; and anti-tumor agents.

Steroidal anti-inflammatory agents such as hydrocortisone, prednisone, fluticasone, predonisolone, triamcinolone, triamcinolone acetonide, dexamethasone, betamethasone, beclomethasone, and beclomethasone dipropionate; non-steroidal anti-inflammatory agents such as acetaminophen, aspirin, aminopyrine, phenylbutazone, mefenamic acid, ibuprofen, diclofenac sodium, indomethacin, colchicine, and probenocid; enzymatic anti-inflammatory agents such as chymotrypsin and bromelain seratiopeptidase; anti-histaminic agents such as diphenhydramine hydrochloride, chloropheniramine maleate and clemastine; anti-allergic agents (antitussive-expectorant antasthmatic agents such as sodium cromoglycate, codeine phosphate, and isoprotereol hydrochloride.

For nasal delivery, the microspheres may be used with an enhancer such as a lysophosphatide. Lysophosphatides are produced by the hydrolysis of phospholipids. Such materials are surface active and form micellar structures. Lysolecithin and other lysophosphatides may be used to act as a potential absorption enhancer for drug delivery and this increase the bioavailability of the active drug. Lysophosphatidylcholine changes the permeability of membranes and allows the increased uptake of proteins and peptides including, for example, insulin, human growth hormone and other products of biotechnology and recombinant DNA methodologies. After administration the lysophosphatides are converted by the cells of the endothelial lining of the mucosa to the intact phosphatides which are normal cell components (see de Vries et al (11). (Lysolecithin itself is also present in cell membranes in very small quantities (12)). This rapid and efficient conversion of lysophosphatides into the complete phosphatide structure leads to much reduced adverse reactions and side effects in terms of irritation and toxicity.

A preferred material which increases bioavailability is the material lysophosphatidylcholine produced from egg or soy lecithin. Other lysophosphatidylcholines that have different acyl groups as well as lyso compounds produced from phosphatidylethanolamines and phosphatidic acid which have similar membrane modifying properties may be used. Acyl carnitines (e.g. Palmitoyl-DL Canitine-chloride) is an alternative.

Other agents that would be appropriate include chelating agents (EGTA, EDTA, alginates), surface active agents (especially non-ionic materials), acyl glycerols, fatty acids and salts, tyloxapol and biological detergents listed in the SIGMA Catalog, 1988, page 316–321. Also agents that modify the membrane fluidity and permeability would be appropriate such as Enamines (e.g. phenylalanine enamine of ethyllacetoacetate), Malonates (e.g. diethyleneoxymethylene malonate), Salicylates, Bile salts and analogues and fusidates. Suitable concentrations would be up to 10%.

The same concept of delivery of a drug incorporated into or onto a bioadhesive microsphere with an added pharmaceutical adjuvant would apply to systems that contained active drug and mucolytic agent, peptidase inhibitors or irrelevant polypetide substrate singly or in combination. A suitably mucolytic would be thiol containing compounds such as Nacetylcysteine and derivatives thereof. Peptide inhibitors include Actinonin, Amastatin, Antipain, Bestatin, Chloroacetyl-HOLeu-Ala-Gly-NH2, Diprotin A and B, Ebelactone A and B, E-64, Leupeptin, Pepstatin A, Phisphoramion, H-Thr-(tBu)-Phe-Pro-Oh. Aprotinin, Kallikrein, Inh.1, Chymostation, Benzamidine, Chymotrypsin Ing.11, trypsin Inh.111-0. Suitable concentrations would be from 0.01 to 5%.

When used in this way, the microspheres should preferably be of a size between 10 and 100 microns.

The microspheres can be administered via the nasal route by standard well known methods such as by using a nasal insufflator device. Examples of these are already employed for commercial powder systems intended for nasal application (e.g. Fisons Lomudal system). Details of other devices can be found in the pharmaceutical literature (see for example Bell, A. Intranasal Delivery Devices, in Drug Delivery Devices Fundamentals and Applications, Tyle P. (ed), Dekker, New York, 1988).

Specifically the microspheres can be used in a delivery system such as that described in our co-pending application PCT/GB88/00396. The microspheres may also be used without an enhancer and specifically in a delivery system as described in our co-pending application PCT/GB88/00836. The use of the microspheres without an enhancer is particularly suitable to enhance the bioavailability of peptide drugs for systemic delivery having a maximum molecular weight of 6000. The microspheres can be delivered by the nasal route as described above.

A BRIEF DESCRIPTION OF THE DRAWINGS

Examples of the invention will now be given with reference to the accompanying figures, in which:

FIG. 1 is a view from above and one side of a stirring paddle;

FIG. 2 is an underneath plan view of the paddle of FIG. 1.

EXAMPLE 1

Hollow, air-filled microspheres were prepared from amylodextrin by the following method.

Primary Emulsion Formulation

A 10% gel was prepared by dispersing 10 g of amylodextrin (soluble potato starch) (Sigma Chemical Company) in 100 ml cold, distilled water. The dispersion was then heated until the dispersion became transparent. This occurred at about 90° C. The gel was allowed to cool while stirring with a magnetic stirrer. 30 ml perfluorohexane (95% Aldrich Chemical Company, Gillingham, Dorset) was added to the cobled gel and homogenised at 7000 rpm for 4 minutes.

Secondary Emulsion Formation 15 ml of the primary emulsion was added to 500 ml soya oil (J. Sainsbury plc) and homogenised at 6000 rpm for 3 minutes.

Fixing the Microspheres

The secondary emulsion was transferred to a hot oil bath (80° C.) and heating continued while stirring at 1500 rpm using a 6-blade paddle stirrer (FIG. 1). The emulsion was heated rapidly at the rate of 2° C. per minute to a maximum bulk emulsion temperature of 100° C., after which it was allowed to cool. The microspheres were then dehydrated by the addition of 200 ml acetone while stirring at 1500 rpm continued.

Harvesting the Microspheres

The microsphere/acetone dispersion was centrifuged at 4000 rpm for 10 minutes. The pellet was collected and resuspended in acetone (Analar, Fisons, Loughborough) The acetone suspension was then filtered through a 1 μm glass microfibre filter and the microspheres collected as a dry cake on the filter circle. The microsphere cake was allowed to air-dry and stored in a desiccator at room temperature. The microspheres could be freeze-dried or not as required.

The particles had a size of 5–20 μm, measured by light microscopy.

EXAMPLE 2

The method is based on the formation of an oil-in-water emulsion. The aqueous phase consisted of an amylodextrin gel and the non-aqueous or oil phase was one of a number of volatile oils. A 10% amylodextrin gel was prepared by dispersing porato amylodextrin or amylodextrin (prepared by the Lintner method) in water and the suspension heated to 80° C. to form a clear gel. A number of volatile oils could be used in the production of the emulsion. These included dichoromethane (b.p. 39°–40° C.), perfluorohexane (b.p. 58°–60° C.), perfluoromethylcyclohexane (b.p. 76°C.), perfluorodimethylcyclohexane (b.p. 101°–102° C.). The oil phase volume was in the range 5–20% (v/v) of the emulsion. A surfactant, Span 80 was added to the emulsion as a stabiliser. The rest of the volume was made up of the amylodextrin gel. The emulsion was homogenised using a Silverson bench top homogeniser at 5000–8000 rpm at room temperature for 2–5 minutes. The emulsion was fixed by heating while stirring (1500 rpm) to a maximum temperature of 120° C. A dehydrating agent such as isopropanol, ethanol or acetone or 20% w/v sodium sulphate (30–50% of total volume) was added to the microspheres which were harvested by centrifugation and filtration. The microspheres were stored in a desiccator at room temperature and the particle diameter determined by light microscopy and laser diffractometry.

Albumin (human serum, bovine serum or egg albumin for example) or its adducts such as HSA-PEG (polyethylene glycol), HSA-PAA (polyamido amide)-PEG could also be added to the amylodextrin gel. 10% w/v aqueous solutions of albumin or its adducts were prepared and added to the amylodextrin gel to make up 5–10% of the gel volume. The preparation was then continued as described above.

Examples 3 to 6 describe the production of hollow or airfilled amylodextrin microspheres using a double emulsion process.

The primary emulsion is an oil-in-water emulsion in which the oil phase is a volatile oil such as perfluorohexane (b.p. 58°–60°C.) and the aqueous or continuous phase is amylodextrin gel in combination with albumin, or albumin-adducts, HSA-PEG (polyethylene glycol), HSA-PAA (polyamido amide)-PEG, Pluronic F-68 may also be added. Other volatile oils such as dichloromethane (b.p. 39°–40° C.), perfluoromethylcyclohexane (b.p. 76° C.), perfluorodimethylcyclohexane (b.p. 101°–102° C.) may also be used.

EXAMPLE 3

10 ml of 1–3% albumin was added to 60 ml of the cooled 10% amylodextrin gel. 20–40 ml of the volatile oil (perfluorohexane) was added to the amylodextrin mixture and homogenised at 6000–8000 rpm for 3 minutes. 15 ml of the emulsion was added to 500 ml of soya oil B.P. containing 5 ml of an anti-foaming agent poly(methylphenyl siloxane). The secondary emulsion was homogenised at 6000–8000 rpm for 3 minutes and fixed by heating in a hot oil bath, while stirring at 1500 rpm to a maximum temperature of 120° C. The mixture was cooled and 200 ml acetone was added to dehydrate the amylodextrin microspheres. The microspheres were harvested by centrifugation and filtration.

EXAMPLE 4

10 ml of 1-3% HSA-PAA-PEG was added to 60 ml of the cooled 10% amylodextrin gel. 20-40 ml of the volatile oil (perfluorohexane; b.p. 58°-60° C.) was added to the amylodextrin mixture and homogenised at 6000-8000 rpm for 3 minutes. 15 ml of the emulsion was added to 500 ml of soya oil B.P. containing 5 ml of an anti-foaming agent poly (methylphenyl siloxane). The secondary emulsion was homogenised at 6000-8000 rpm for 3 minutes and fixed by heating in a hot oil bath, while stirring at 1500 rpm to a maximum temperature of 120° C. The mixture was cooled and 200 ml acetone was added to dehydrate the amylodextrin microspheres. The microspheres were harvested by centrifugation and filtration.

EXAMPLE 5

10 ml of 1-3% HSA-PEG was added to 60 ml of the cooled 10% amylodextrin gel. 20-30 ml of the volatile oil (perfluorohexane) was added to the amylodextrin mixture and homogenised at 6000-8000 rpm for 3 minutes. 15 ml of the emulsion was added to 500 ml of soya oil B.P. containing 5 ml of an anti-foaming agent poly(methylphenyl siloxane). The secondary emulsion was homogenised at 6000-8000 rpm for 3 minutes and fixed by heating in a hot oil bath, while stirring at 1500 rpm to a maximum temperature of 120° C. The mixture was cooled and 200 ml acetone was added to dehydrate the amylodextrin microspheres. The microspheres were harvested by centrifugation and filtration.

EXAMPLE 6

10 ml of 1-3% Pluronic F-68 was added to 60 ml of the cooled 10% amylodextrin gel. 20-40 ml of the volatile oil (perfluorodecalin) was added to the amylodextrin mixture and homogenised at 6000-8000 rpm for 3 minutes. 15 ml of the emulsion was added to 500 ml of soya oil B.P. containing 5 ml of an anti-foaming agent poly(methylphenyl siloxane). The secondary emulsion was homogenised at 6000-8000 rpm for 3 minutes and fixed by heating in a hot oil bath, while stirring at 1500 rpm to a maximum temperature of 120° C. The mixture was cooled and 200 ml acetone was added to dehydrate the amylodextrin microspheres. The microspheres were harvested by centrifugation and filtration.

Examples 7 and 8 describe the preparation of hollow albumin microspheres incorporating albumin adducts.

EXAMPLE 7

60 ml of a 10% aqueous solution of albumin (HSA) was prepared and added to 40 ml of a volatile oil such as perfluorohexane. The mixture was homogenised at 6000-8000 rpm for 3 minutes using a bench top Silverson homogeniser. 5 ml polymethylphenyl siloxane was added to 500 ml soya oil B.P. and stirred thoroughly. 15 ml of the albumin emulsion was added to the soya oil and homogenised at 6000-8000 rpm for 3 minutes. The emulsion was heated in an oil bath, while stirring at 1500 rpm with a paddle stirrer to a maximum temperature of 115° C. for 15 minutes. After cooling, petroleum ether was added to the mixture and the microspheres were harvested by centrifugation and filtration.

EXAMPLE 8

A 10% aqueous solution of albumin (HSA) of which 5-10% of the total protein was an albumin adduct such as HSA-PEG (polyethylene glycol) or HSA-PAA (polyamido amide)-PEG was prepared. 60 ml of the albumin solution was added to 40 ml of a volatile oil such as perfluorohexane (b.p. 58°-60° C.) and homogenised at 6000-8000 rpm for 3 minutes using a bench top Silverson homogeniser. 5 ml polymethylphenyl siloxane was added to 500 ml soya oil B.P. and stirred thoroughly. 15 ml of the albumin emulsion was added to the soya oil and homogenised at 6000 rpm for 3 minutes. The emulsion was heated in an oil bath, while stirring at 1500 rpm with a paddle stirrer to a maximum temperature of 115° C. for 15 minutes. After cooling, petroleum ether was added to the mixture and the microspheres were harvested by centrifugation and filtration.

Other volatile oils such as dichloromethane (b.p. 39°-40° C.), perfluoromethylcyclohexane (b.p. 76° C.), perfluorodimethylcyclohexane (b.p. 101°-102° C.) may also be used.

EXAMPLE 9

Solid microspheres were prepared from amylodextrin by the following method.

Primary Emulsion Formulation

A 10% starch gel was prepared by dispersing 10 g of amylodextrin potato starch (Sigma Chemical Company) in 100 ml cold, distilled water. The dispersion was then heated until the dispersion became transparent. This occurred at about 90° C. . The gel was allowed to cool while stirring with a magnetic stirrer. 10 ml perfluorohexane (95% Aldrich Chemical Company, Gillingham, Dorset) was added to the cooled gel and homogenised at 7000 rpm for 4 minutes or passed through a microfluidizer.

Secondary Emulsion Formation 15 ml of the primary emulsion was added to 500 ml soya oil (J. Sainsbury plc) and homogenised at 6000 rpm for 3 minutes.

The fixing and harvesting of the microspheres was as described in Example 1.

EXAMPLE 10

Solid human serum albumin microspheres were prepared using a double emulsion method. The microspheres were solid and the mean diameter could be varied between 1 μm and 30 μm depending on the manufacturing conditions.

Preparation of the Primary Emulsion 10 ml of Perfluorohexane 20 ml of 10% human serum albumin (Albutein 25%: Alpha Therapeutics). The albumin solution and perfluorohexane were mixed and passed through the Microfluidiser operating at 14000 psi through 3 cycles. A cooling coil packed with ice was fitted to ensure that the temperature of the emulsion did not rise above 40° C. Temperatures of 50° C. and above caused the emulsion to foam excessively and accelerated its destabilisation.

Preparation of the Secondary Emulsion 15 ml of the primary emulsion was added to 500 ml soya oil and homogenised at 6800 rpm for 3 minutes.

Fixing and Harvesting the Microspheres

The secondary emulsion was transferred to an oil bath and the temperature increased very slowly (1° C. per minute).

The emulsion was stirred with a 6-blade stirrer operating at 1500 rpm. The stirrer blade was positioned so that the head was located 4 cm below the surface of the emulsion. The temperature of the emulsion was allowed to rise to 120° C. where it equilibrated for 20 minutes.

Harvesting the Microspheres

The emulsion was allowed to cool and 200 ml of petroleum ether was added. The mixture was then centrifuged at 4500 rpm for 20 minutes and the pellet was collected. The pellet was resuspended in ether and passed through a 1 μm Fluoropore filter. The filter cake was washed in ethanol and acetone respectively. The suspension was then filtered again and the filter-cake allowed to air-dry in a desiccator at room temperature. The microspheres could be freeze-dried or not as required.

We claim:

1. A double emulsion process for preparing hollow microcapsules, the process comprising
   a) combining a volatile oil with an aqueous phase comprising a water soluble material selected from the group consisting of a polyethylene glycol (PEG) conjugate other than PEG conjugated to a water soluble modified starch, a water soluble starch other than hydroxyethyl starch, and a proteinaceous material, to form a primary emulsion,
   b) combining the primary emulsion with a second oil, to form a secondary emulsion,
   c) maintaining the secondary emulsion under conditions wherein the material forms microcapsules containing a liquid core comprising the volatile oil, and
   d) removing at least some of the volatile oil during or after step c), to form hollow microcapsules.

2. A process according to claim 1 further comprising making the microcapsules water-insoluble by a process selected from the group consisting of chemical denaturation, heat denaturation, chemical crosslinking, chelating or grafting of the microcapsules.

3. A process according to claim 1 wherein the material is a modified starch selected from the group consisting of amylodextrin, amylopectin and carboxymethyl starch.

4. A process according to claim 1 wherein the material is a PEG conjugate selected from the group consisting of a PEG-protein conjugate and a PEG-starch conjugate.

5. A process according to claim 1 wherein the volatile oil has a boiling point between 20°–100° C.

6. A process according to claim 5 wherein the volatile oil is removed from the oil-filled capsules by evaporation.

7. A process according to claim 6 wherein the volatile oil is removed by heating the microcapsules.

8. A process according to claim 2 further comprising dehydrating the microcapsules and freeze-drying the microcapsules.

9. Microcapsules prepared by the process of claim 1, 2 or 3.

10. Solid microspheres for use in delivery systems, the microspheres having been formed by
    a) combining a volatile oil with an aqueous phase comprising a water soluble material selected from the group consisting of a polyethylene glycol (PEG) conjugate other than PEG conjugated to a water soluble modified starch, a water soluble starch other than hydroxyethyl starch, and a proteinaceous material, to form a primary emulsion,
    b) combining the primary emulsion with a second oil, to form a secondary emulsion,
    c) maintaining the secondary emulsion under conditions wherein the material forms a wall around a liquid core comprising the volatile oil, and
    d) removing the volatile oil in step c) before the material hardens, to form microspheres.

11. An air-filled microcapsule for use in diagnostic procedures, the air-filled microcapsule having been formed by
    a) combining a volatile oil with an aqueous phase comprising a water soluble material selected from the group consisting of a polyethylene glycol (PEG) conjugate other than PEG conjugated to a water soluble modified starch, a water soluble starch other than hydroxyethyl starch, and a proteinaceous material, to form a primary emulsion,
    b) combining the primary emulsion with a second oil, to form a secondary emulsion,
    c) maintaining the secondary emulsion under conditions wherein the material forms microcapsules containing a liquid core comprising the volatile oil, and
    d) removing at least part of the volatile oil during or after step c), to form hollow air-filled microcapsules.

12. A pharmaceutical composition for administration to the body comprising solid microspheres or air-filled microcapsules according to claim 10 or 11 and a pharmaceutically acceptable carrier.

13. A method of forming a diagnostic image comprising injecting the air-filled microcapsules according to claim 11 into the bloodstream of a patient, reflecting ultrasonic waves off the microcapsules as they pass through or lodge in an organ to be imaged and forming an image from the reflected waves.

14. A double emulsion process for forming solid microspheres, the process comprising:
    a) combining a volatile oil with an aqueous phase comprising a water soluble material selected from the group consisting of a polyethylene glycol (PEG) conjugate other than PEG conjugated to a water soluble modified starch, a water soluble starch other than hydroxyethyl starch, and a proteinaceous material, to form a primary emulsion,
    b) combining the primary emulsion with a second oil, to form a secondary emulsion,
    c) maintaining the secondary emulsion under conditions wherein the material forms microspheres, and
    d) removing the volatile oil during step c) before the material hardens, to form solid microspheres.

15. The process of claim 14 wherein the volatile oil has a boiling point between 20°–100° C., and wherein the volatile oil is removed by evaporation upon the application of heat to the microspheres.

16. The process of claim 14 wherein the material is a modified starch selected from the group consisting of amylodextrin, amylopectin and carboxymethyl starch.

* * * * *